United States Patent [19]

Enloe

[11] Patent Number: 4,501,587
[45] Date of Patent: Feb. 26, 1985

[54] DISPOSABLE DIAPER HAVING IMPROVED ABSORBENT PAD ARRANGEMENT

[75] Inventor: Kenneth M. Enloe, Winnebago County, Wis.

[73] Assignee: Kimberly-Clark Corporation, Neenah, Wis.

[21] Appl. No.: 430,621

[22] Filed: Sep. 30, 1982

[51] Int. Cl.³ .............................................. A61F 13/16
[52] U.S. Cl. ................................................... 604/385
[58] Field of Search ............... 604/385, 358, 397, 398, 604/393, 378

[56] References Cited

U.S. PATENT DOCUMENTS

| | | | |
|---|---|---|---|
| 3,658,063 | 4/1972 | Schaar | 604/385 |
| 3,710,797 | 1/1973 | Marsan | 604/385 |
| 3,765,418 | 10/1973 | Jones, Sr. | 604/385 |
| 3,924,626 | 12/1975 | Lee et al. | 604/385 X |
| 4,285,342 | 8/1981 | Mesek | 604/385 |

Primary Examiner—John D. Yasko
Attorney, Agent, or Firm—James P. O'Shaughnessy; R. Jonathan Peters

[57] ABSTRACT

A disposable diaper absorbent pad assembly is disclosed in which a main absorbent pad has longitudinal fold portions folded toward the longitudinal centerline of the diaper and a first auxiliary absorbent pad positioned in the front section of the diaper in the space between the longitudinal fold portions. A second auxiliary absorbent pad is positioned between the main pad and the first auxiliary pad and has a width slightly less than the width between the fold lines of the longitudinal fold portions. The two auxiliary pads increase the absorbent capacity of the diaper in the front section where most necessary and the first auxiliary pad utilizes a folded space which is otherwise wasted. Both auxiliary pads assist in uniform, non-distorted folding of the diaper to provide a pleasing folded appearance and minimize packaging problems.

13 Claims, 10 Drawing Figures

DISPOSABLE DIAPER HAVING IMPROVED ABSORBENT PAD ARRANGEMENT

FIELD OF THE INVENTION

This invention relates to a disposable diaper having auxiliary absorbent pad material positioned to increase absorbent capacity and facilitate folding of the diaper. More particularly, the invention relates to the positioning of additional absorbent material in the front section of the diaper in a space that has not heretofore been utilized to maintain or increase the absorbent capacity of the diaper while at the same time decreasing the folded thickness of the diaper so that it occupies less space.

BACKGROUND OF THE INVENTION

Disposable diapers typically have a substantially rectangular absorbent pad and side portions that are folded toward each other, that is, toward the longitudinal centerline of the diaper and against the pad. However, the fold portions are usually positioned such that the opposing edges of the fold portions do not reach each other, but are spaced apart. Where the fold portions include pad material, a space between the folded edges having a thickness approximately equal to the thickness of the pad material in the fold portions is formed between the fold portions. In those types of diapers in which the pad is shaped or contoured to form a narrower portion to allow space for the wearer's legs, the volume of the void space between the opposite edges of the fold portions increases substantially. In addition to the longitudinal side portions being folded toward each other and against the central portion of the diaper, for purposes of packaging, the front and rear sections of the diaper are folded into engagement with each other along a transverse line dividing the diaper into front and rear sections. The void spaces between the longitudinal fold portions in the front section and in the rear section of the diaper are thus combined to form a single larger void space in the fully folded diaper which, to the extent that it is retained after the diaper is placed in a package, is wasted space. To the extent that the folded diaper is compressed to eliminate the void space, the diaper is distorted to decrease absorbent capacity, to detract from the appearance of the diaper and create packaging problems when using automatic high-speed packaging equipment. A related folding problem involves the folding of the side portions, including the absorbent material they contain, consistently along a longitudinal fold line, to provide a uniform width diaper when fully folded. Similar to folding of the front and rear sections of the diaper together, uniform folding of the diaper side portions enhances the appearance of the diaper and minimizes packaging problems.

Another problem which is common to disposable diapers is the need for increased fluid absorbent capacity. One of the areas of the diaper at which it is particularly important to have a large amount of absorbent capacity is in the front portion of the diaper because this is the area normally directly wetted by infants and because of the tendency of urine to flow to this area of the diaper when the baby is crawling or sleeping. There have been a wide variety of suggested solutions for increasing the absorbent capacity of the diaper in general and increasing the absorbent capacity of the diaper in the frontal region in particular. Typical of these is the arrangement illustrated in U.S. Pat. No. 3,926,189 to Taylor. This patent discloses a main pad having an auxiliary portion extending from the main pad at approximately the transverse centerline of the diaper. The auxiliary pad portion may be folded forward to the front area of the diaper when the baby is in a sleeping position or the diaper is to be worn by a boy baby to thereby gain the increased front absorbent capacity.

It is a principal object of this invention to locate or distribute absorbent pad material that is auxiliary to the main absorbent pad of a disposable diaper at positions which assist in folding the diaper to a uniform size and shape and utilize void spaces for absorbent material to increase the absorbent capacity of the diaper or maintain the absorbent capacity of the diaper while providing a thinner less bulky overall diaper.

SUMMARY OF THE INVENTION

The invention is accomplished by providing a disposable diaper comprising a main pad assembly having a liquid impervious cover sheet, a liquid pervious liner sheet opposite the cover sheet, a main absorbent pad disposed between the liner and cover sheets and in which the main pad assembly, when the diaper is in at least a partially folded condition has a pair of longitudinal fold portions extending toward the longitudinal centerline of the diaper and spaced apart opposed edges defining a space between the fold portions in which an auxiliary absorbent pad is positioned. A second auxiliary absorbent pad having longitudinal edges adjacent to the fold lines of the longitudinal fold portions may be positioned between the aforementioned auxiliary absorbent pad and the main absorbent pad in the front section of the diaper. The second auxiliary pad will provide a fold guide and support for folding the longitudinal fold portions and will provide additional absorbent capacity in the front section of the diaper.

DESCRIPTION OF THE DRAWINGS

Further objects and advantages of the invention will appear when taken in conjunction with the accompany drawings in which.

DETAILED DESCRIPTION OF THE INVENTION

Figure 1:
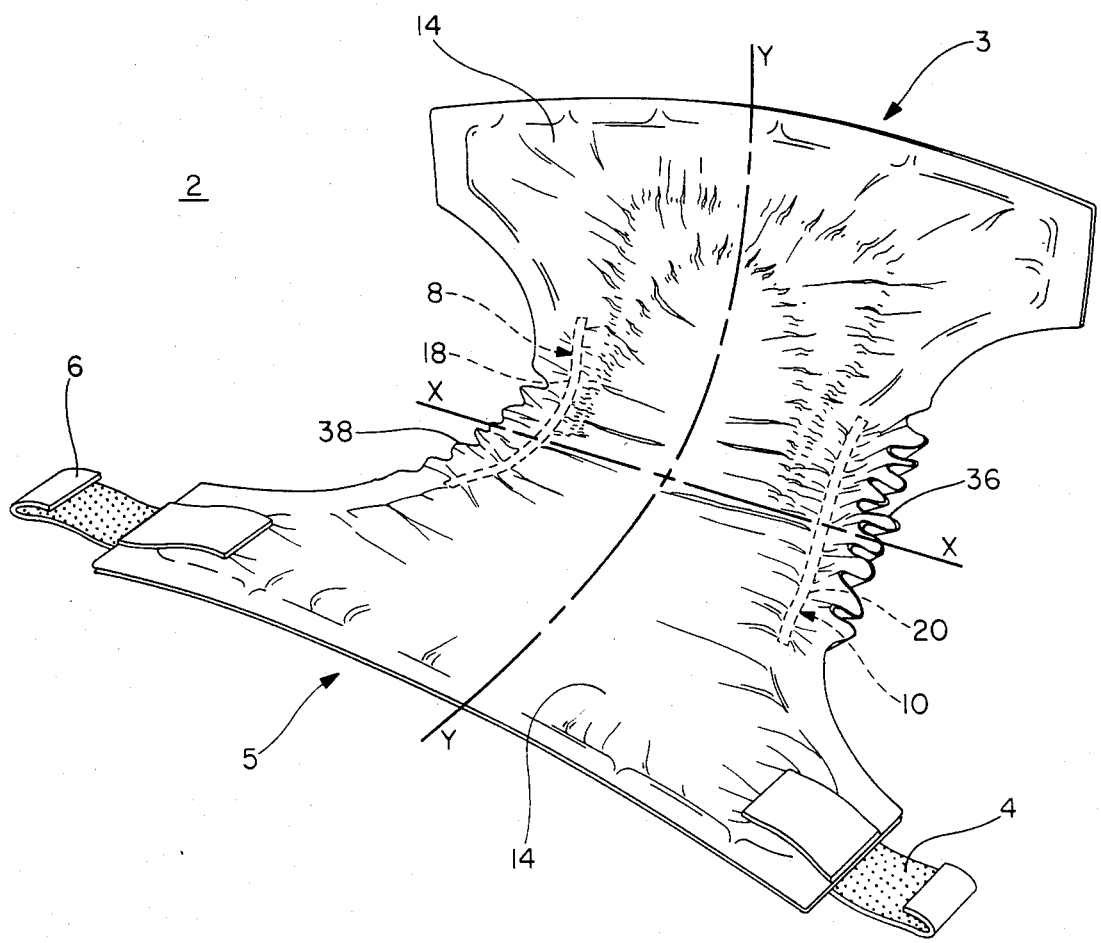
FIG. 1 is a perspective view of a disposable diaper just prior to its fitting onto a wearer with the liner sheet partially broken away.
Figure 2:
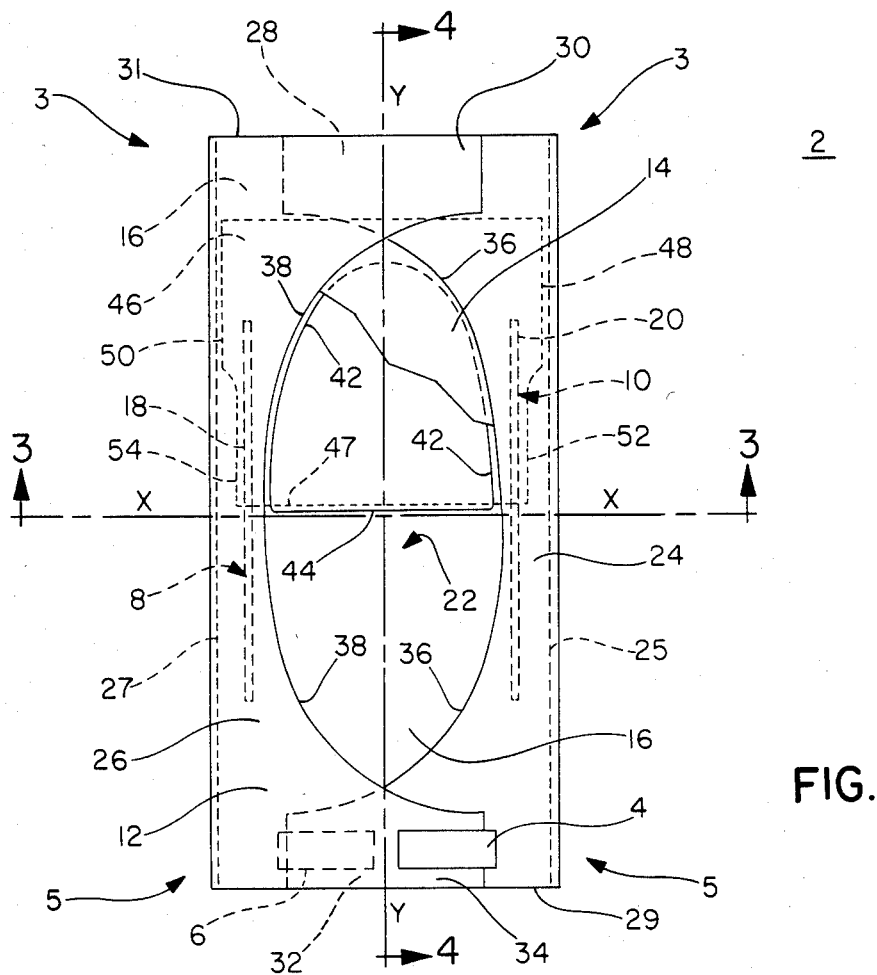
FIG. 2 is a plan view of a partially folded disposable diaper utilizing the absorbent pad distribution according to the invention.

With reference to the drawings, the disposable diaper shown in FIG. 1 is in an unfolded condition ready to be fitted on to a wearer and in FIGS. 2-8 the diaper is shown in a partial or fully folded condition. The disposable diaper is shown as having a main pad assembly 2 and a pair of waist fastening tapes 4 and 6. As shown in the embodiments of FIGS. 1 and 2, the diapers may also have leg elastic means 8 and 10.

Figure 6:
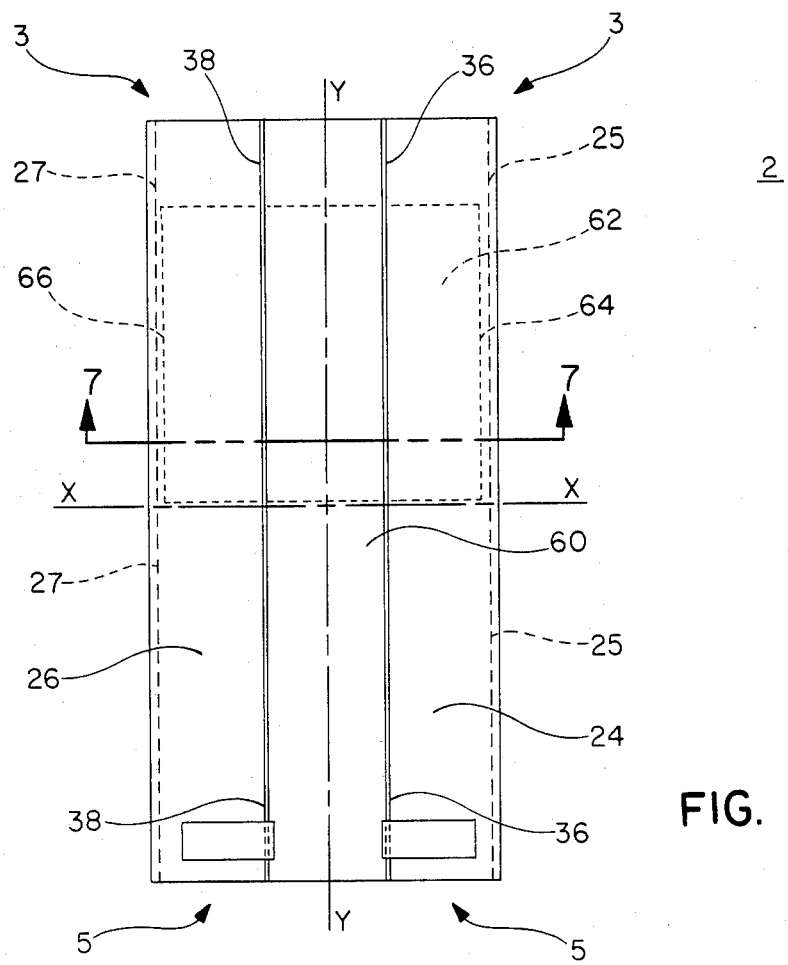
FIG. 6 is a plan view of a disposable diaper illustrating an alternative embodiment of the invention.

As shown in FIG. 1, the diaper has a longitudinal centerline Y—Y and a transverse centerline X—X running through a crotch section and delineating the front section 3 and the rear section 5 of the diaper. The waist fastening tapes 4 and 6 are shown in FIG. 1 in an extended condition ready to be attached to the front section 3 of the diaper when it is placed on a wearer. In FIGS. 2 and 6 the waist fastening tapes 4 and 6 are shown in a closed condition, prior to use of the diaper. The leg elastic means 8 and 10 comprise lengths of elastic material 18 and 20 attached to the cover sheet 12 or the liner sheet 14, or both, and positioned between the cover sheet and the liner sheet substantially parallel to the longitudinal centerline Y—Y of the diaper.

Figure 3:
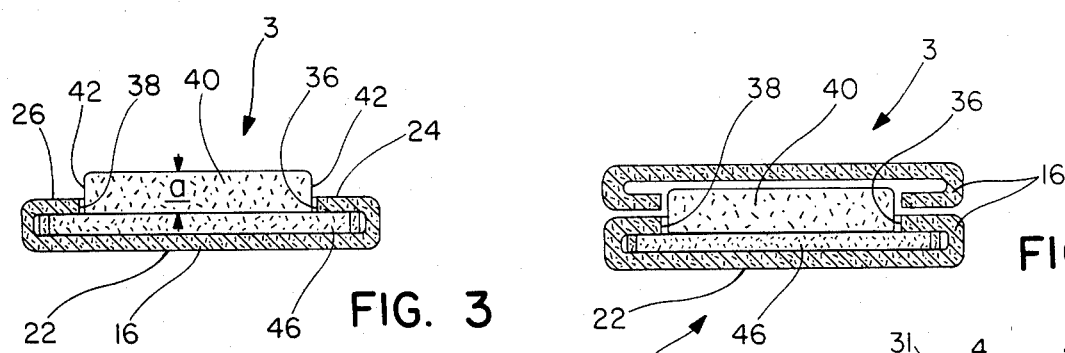
FIG. 3 is an end elevation, cross-sectional view along the line 3—3 of FIG. 2.
Figure 3A:
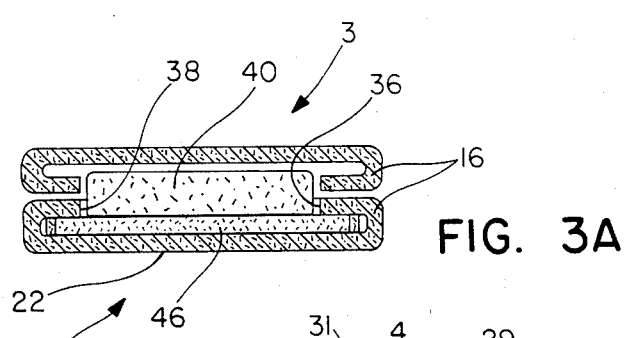
FIG. 3A is a simplified end elevation, cross-sectional view similar to that of FIG. 3, in which the diaper is fully folded and the front and back sections of the diaper are in engagement with each other.
Figure 4:
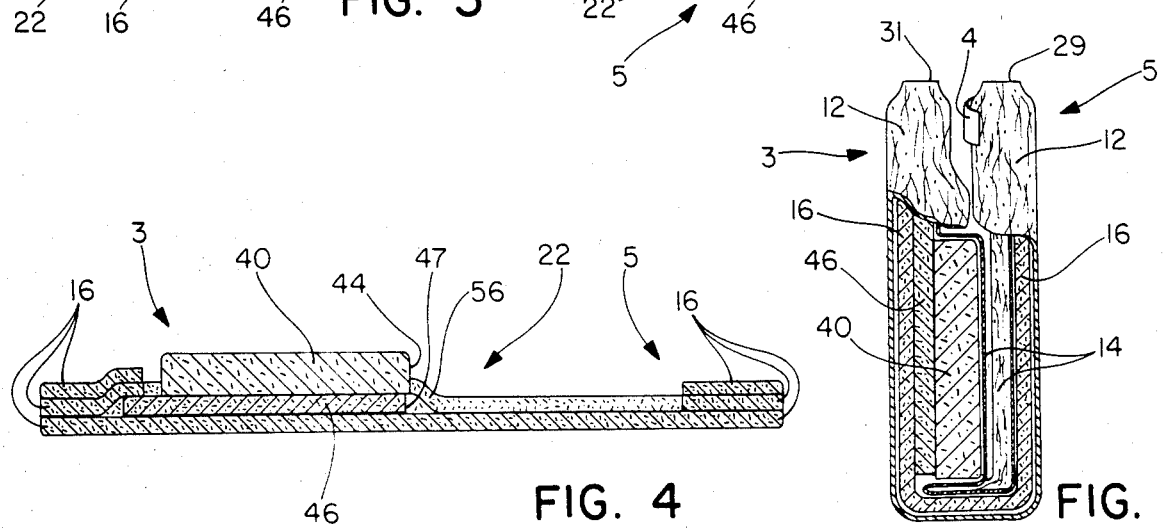
FIG. 4 is a simplified side elevation, cross-sectional view along the line 4—4 of FIG. 2.

The main pad assembly includes a cover sheet 12, a liquid pervious body side liner sheet 14 positioned opposite and generally parallel to the cover sheet 12, and a main absorbent pad 16 disposed between the liner and cover sheets and having an area slightly less than that of the liner and cover sheets so that the latter engage each other around the periphery of the absorbent pad 16. The main pad assembly 2 further includes a central portion 22 and longitudinal fold portions 24 and 26 when the diaper is in a partially folded condition as shown in FIGS. 2-4. The fold portions 24 and 26 are respectively folded along fold lines 25 and 27 as shown in FIG. 2. The main pad assembly 2 also includes ear portions 28 and 30 in the front section 3 of the diaper and ear portions 32 and 34, on which waist fastening tapes 4 and 6 are respectively mounted, in the rear section 5 of the diaper. The longitudinal fold portions 24 and 26 have opposed edges 36 and 38 which, throughout most of their length, are spaced apart to define a space between the fold portions. The edges 36 and 38 may have a concave contour intermediate the ends 29 and 31 of the diaper directed toward the longitudinal centerline when the diaper is unfolded as shown in FIG. 1.

Figure 5:
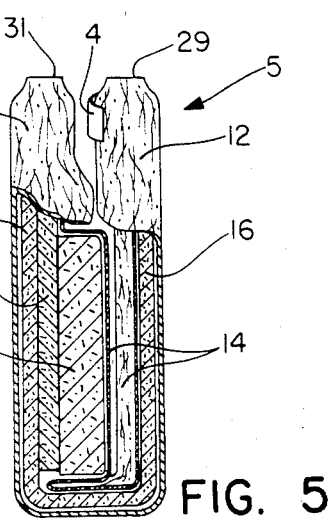
FIG. 5 is a simplified side elevation view, partially in cross-section, showing the diaper of FIG. 2 in a fully folded condition.

The diaper also includes a first auxiliary absorbent pad 40 positioned between the opposed edges 36 and 38 of the fold portions in the spaced defined by the edges 36 and 38. The auxiliary pad 40 has an edge 42 adjacent to the edges 36 and 38 of the fold portions 24 and 26 which follows the contour of the edges 36 and 38 and a transverse edge 44 adjacent to the transverse centerline X—X of the diaper. The auxiliary pad 40 is thus positioned only in the front section 3 of the diaper. As is illustrated in FIG. 3, the auxiliary pad 40 has a thickness a and extends out of the space between the fold portions 24 and 26 when the diaper is in the partially folded condition as illustrated in FIGS. 2-4. The thickness a of the pad 40 is sufficient such that, when the diaper is in the fully folded condition as shown in FIGS. 5 and 5A, the auxiliary pad 40 extends from the liner 14 in the front section 3 to the liner 14 in rear section 16 fills substantially the entire volume of the space between the edges 36 and 38 of the fold portions 24 and 26. Most typically, the thickness a will be double the maximum thickness of fold portions 24 or 26 where the fold portions have same maximum thickness in both the front section 3 and the rear section 5 of the diaper. Alternatively, where the fold portions 24 and 26 are symmetrical about the longitudinal centerline Y—Y, the thickness a will be equal to the total thickness of the fold portions 24 or 26 in the front section 3 and the rear section 5 of the diaper.

The diaper also includes a second auxiliary absorbent pad 46 positioned in engagement with the central portion 22 of the main pad assembly 2 preferably only in the front section 3 of the diaper. The absorbent pad 46 has a transverse edge 47 and edges 48 and 50 adjacent to and following the fold lines 25 and 27 of longitudinal fold portions 24 and 26 which provide support and guidance for the folding of the fold portions 24 and 26 along their fold lines 25 and 27. The edges of the absorbent pad 46 diverge from the fold lines 25 and 27 in the crotch section 7 such that the pad 46 has a narrower width at its end most adjacent the transverse centerline X—X as identified by the edges 52 and 54. The contour defined by each of the edges 52 and 54 provide a better fit and more comfort in the leg areas of the diaper. The absorbent pad 46 provides greater fluid absorbent capacity in the front section 3 of the diaper where such extra capacity is most desirable. At the same time, the terminating of the pad 46 along transverse edge 47 and pad 40 along transverse edge 44 at approximately the transverse centerline X—X provides a void 56 for containing fecal matter between the central portion 22 of the main pad assembly 2 and the skin of the wearer.

Figure 7:
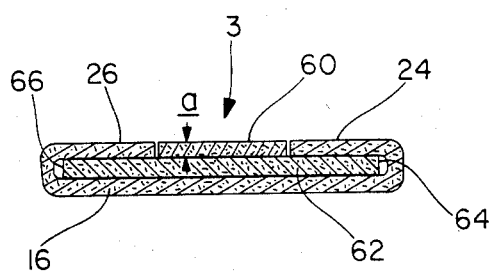
FIG. 7 is a simplified end elevation, cross-sectional view, through the line 7—7 of FIG. 6.
Figure 8:
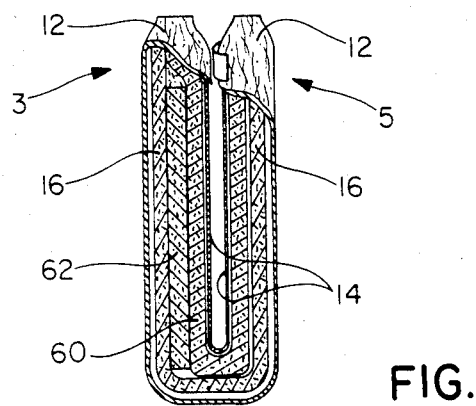
FIG. 8 is a simplified side elevation view, partially in cross-section, showing the diaper illustrated in FIG. 6 in a fully folded condition.

In FIGS. 6-8, a second embodiment of the invention is illustrated in which elements that are substantially similar to the elements of the embodiment illustrated in FIGS. 2-5 are identified with the same numerals. The main pad assembly 2 of the diaper shown in FIGS. 6-8 has longitudinal fold portions 24 and 26 in which the opposing edges 36 and 38 are spaced apart along the entire longitudinal length of the main pad assembly 2. The opposed edges 36 and 38 are shown as being substantially parallel to each other along the entire length of the main pad assembly 2, however, it is not intended that the edges 36 and 38 be necessarily limited to a parallel relationship.

Figure 7A:
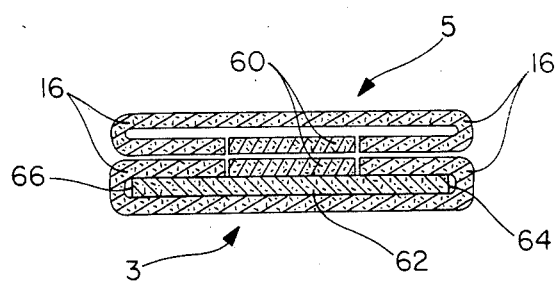
FIG. 7A is a simplified end elevation, cross-sectional view similar to that of FIG. 7, showing the diaper of FIG. 6 in a fully folded condition.

The first auxiliary absorbent pad 60 of the diaper shown in FIGS. 6-8, extends from the front section 3 into the rear section 5 of the diaper and is not limited to being located only in the front section 3 of the diaper. As shown in FIG. 6, the absorbent pad 60 runs the full longitudinal length of the diaper. Since the absorbent pad 60 extends into the rear section 3 of the diaper as well as the into front section 5, it therefore will have a thickness when folded equal to the total of its thickness in the rear section 3 and its thickness in the front section 5, as shown in FIG. 7A. The pad 60 has an unfolded thickness a equal only to the maximum thickness of the adjacent longitudinal fold portions 24 and 26, as shown in FIG. 7. Similarly to the auxiliary absorbent pad 40 of the embodiment of FIGS. 2-5, the absorbent pad 60 provides additional absorbent capacity for the diaper by utilizing a space otherwise not used while at the same time permitting an overall less bulky diaper and a diaper having a better appearance when fully folded.

The diaper of FIGS. 6-8 also may include a second auxiliary absorbent pad 62 positioned preferably only in the front section 3 of the diaper. The lateral edges 64 and 66 of the pad 62 are positioned along their full longitudinal length adjacent to the fold lines 25 and 27 of the longitudinal fold portions 24 and 26 to provide guidance and support during folding of the fold portions 24 and 26.

An arrangement of absorbent pad material in a disposable diaper has been described which both provides increased absorbent capacity where most necessary and assists in providing a uniform, non-distorted diaper shape which facilitates packaging of the diaper and gives it a pleasing folded appearance. In addition, the adding of absorbent material in the void space in the front section of the diaper to absorb an increased percentage of fluid permits decreasing the volume of the main absorbent pad of the diaper while maintaining or increasing the total amount of fluid which can be absorbed by the diaper. The main pad can thus be thinner to produce a diaper which is less bulky and therefore more comfortable to the wearer and which occupies less packaging space.

It will be understood that the foregoing description of the present invention is for purposes of illustration only and that the invention is susceptible of a number of modifications or changes, none of which entail any departure from the spirit and scope of the present invention as defined in the hereto appended claims. For example, the auxiliary pads of the invention may be either separately formed and subsequently assembled or formed integrally as a single piece in the final shape.

What is claimed is:

1. A disposable diaper comprising, in combination:
   a crotch area;
   a main pad assembly having a transverse fold line in the crotch area dividing the diaper into front and rear sections, a liquid impervious cover sheet, a liquid pervious liner sheet opposite the cover sheet, and a main absorbent pad disposed between the liner and cover sheets;
   the main pad assembly, when the diaper is in at least a partially folded condition, having a pair of longitudinal fold portions extending toward the longitudinal centerline of the diaper, said fold portions including a portion of the main absorbent pad and having spaced apart opposed edges defining a space between the fold portions; and
   an auxiliary absorbent pad positioned between the opposed edges of the fold portions in said space only in said front section and said diaper.

2. The combination according to claim 1 wherein the auxiliary pad has a thickness equal to the distance between the liner sheet in the front section and the liner sheet in the rear section when the diaper is fully folded.

3. The combination according to claim 1 wherein the auxiliary pad has a thickness equal to the total thickness of the main absorbent pad laterally most adjacent to the auxiliary pad in the front and rear sections of the diaper.

4. The combination according to claim 1 wherein the auxiliary pad has a thickness equal to twice the maximum thickness of one of the fold portions.

5. The combination according to claim 2, 3 or 4 further comprising:
   another auxiliary absorbent pad positioned in the front section of the diaper between the main absorbent pad and absorbent pad positioned in said space; and wherein
   both of the auxiliary absorbent pads have a transverse edge contiguous to the transverse fold line whereby a void for containing fecal matter is formed in the rear section.

6. The combination according to claims 1 wherein the longitudinal fold portions each have opposite ends and define said space only intermediate said ends.

7. The combination according to claim 6 wherein:
   said edge of each longitudinal fold portion has a predetermined contour; and
   the auxiliary absorbent pad has an edge adjacent to and following the contour of the edge of each fold portion.

8. The combination according to claim 7 wherein said contour is concave toward the longitudinal centerline of the diaper intermediate the opposite ends of the longitudinal fold portions.

9. The combination according to claim 8 wherein each longitudinal fold portion contains a portion of the main absorbent pad along the concave contour edge of the fold portion.

10. A disposable diaper comprising, in combination:
    a crotch area;
    a main pad assembly having a liquid impervious cover sheet, a liquid pervious liner sheet opposite the cover sheet, and a main absorbent pad disposed between the liner and cover sheets;
    the main pad assembly, when the diaper is in a folded condition, having a pair of longitudinal fold portions each folded along a fold line running through the main absorbent pad, said fold portions extending toward the longitudinal centerline of the diaper and having spaced apart opposed edges defining a space between the fold portions;
    a first auxiliary absorbent pad engaging the main absorbent pad and being positioned between opposed edges of the fold portions in said space; and
    a second auxiliary absorbent pad between the main absorbent pad and the first absorbent pad, said second auxiliary pad having a pair of edges each adjacent to and diverging from a fold line toward said longitudinal centerline of a fold portion whereby the second auxiliary pad provides edge support for forming the fold portion about the fold line.

11. The combination according to claims 10 wherein:
    the diaper has a crotch area;
    the main pad assembly has a transverse fold line in the crotch area dividing the diaper into front and rear sections; and
    said second auxiliary absorbent pad is positioned only in the front section of the diaper.

12. The combination according to claim 11 wherein the first and second auxiliary pads each have a transverse edge contiguous to the transverse fold line whereby a void for containing fecal matter is formed in the rear section adjacent the fold line.

13. The combination according to claims 10 wherein the first auxiliary pad has a thickness equal to the distance between the liner sheet in the front section and the liner sheet in the rear section when the diaper is fully folded.

* * * * *

UNITED STATES PATENT AND TRADEMARK OFFICE
CERTIFICATE OF CORRECTION

PATENT NO. : 4,501,587
DATED : February 26, 1985
INVENTOR(S) : Kenneth M. Enloe

It is certified that error appears in the above-identified patent and that said Letters Patent are hereby corrected as shown below:

Column 1, Line 29, insert after "narrower", the following --central--.

Column 3, Line 13, correct the spelling of ."diapers" to read --diaper--.

Column 3, Lines 62 and 64, the word "a" should be italicized.

Column 4, Lines 3, 9, and 59, the word "a" should be italicized.

Signed and Sealed this

Twenty-seventh Day of August 1985

[SEAL]

Attest:

DONALD J. QUIGG

Attesting Officer       Acting Commissioner of Patents and Trademarks